(12) United States Patent
De Laat et al.

(10) Patent No.: US 9,383,195 B2
(45) Date of Patent: Jul. 5, 2016

(54) LITHOGRAPHIC APPARATUS AND METHOD

(75) Inventors: Wilhelmus Johannes Maria De Laat, Heeswijk-Dinther (NL); Cheng-Qun Gui, Best (NL); Peter Theodorus Maria Giesen, Geldrop (NL); Marcus Theodoor Wilhelmus Van Der Heijden, Dilsen-Stokkem (BE); Erwin Rinaldo Meinders, Veldhoven (NL); Mária Péter, Eindhoven (NL)

(73) Assignee: ASML NETHERLANDS B.V., Veldhoven (NL)

( * ) Notice: Subject to any disclaimer, the term of this patent is extended or adjusted under 35 U.S.C. 154(b) by 898 days.

(21) Appl. No.: 12/741,733

(22) PCT Filed: Nov. 3, 2008

(86) PCT No.: PCT/IB2008/002977
§ 371 (c)(1),
(2), (4) Date: Jul. 26, 2012

(87) PCT Pub. No.: WO2009/060294
PCT Pub. Date: May 14, 2009

(65) Prior Publication Data
US 2012/0281192 A1    Nov. 8, 2012

Related U.S. Application Data

(60) Provisional application No. 60/996,279, filed on Nov. 8, 2007.

(51) Int. Cl.
*G03F 7/20* (2006.01)
*G01B 11/30* (2006.01)
*G01N 21/956* (2006.01)

(52) U.S. Cl.
CPC .............. *G01B 11/306* (2013.01); *G03F 7/703* (2013.01); *G03F 7/7085* (2013.01); *G03F 7/70783* (2013.01); *G01N 2021/95676* (2013.01)

(58) Field of Classification Search
CPC .. G01B 11/306; G01B 11/303; G01B 11/285; G01N 21/94; G01N 21/9501; G03F 7/703; G03F 7/70783; G03F 7/7085; G03G 15/5029
USPC ................. 355/30, 53; 356/601, 237.1–237.5
See application file for complete search history.

(56) References Cited

U.S. PATENT DOCUMENTS 4,589,773 A * 5/1986 Ido et al. ....................... 356/623
5,191,200 A * 3/1993 van der Werf et al. ..... 250/201.4
(Continued)

FOREIGN PATENT DOCUMENTS

| EP | 0 984 245 A2 | 3/2000 |
| EP | 1 452 851 A1 | 9/2004 |

(Continued)

OTHER PUBLICATIONS

International Search Report for PCT/IB2008/002977.
(Continued)

*Primary Examiner* — Steven H Whitesell Gordon
(74) *Attorney, Agent, or Firm* — Pillsbury Winthrop Shaw Pittman LLP

(57) ABSTRACT

A method of obtaining information indicative of the topography of a surface of a flexible substrate, the method including directing a beam of radiation at the surface of the flexible substrate; and detecting changes in intensity distribution, or angle of reflection, of the beam of radiation after the beam of radiation has been reflected from the surface of the substrate to obtain information indicative of the topography of the surface of the flexible substrate.

21 Claims, 4 Drawing Sheets

(56) References Cited

U.S. PATENT DOCUMENTS

| | | | |
|---|---|---|---|
| 5,521,692 A | | 5/1996 | Bares |
| 5,559,582 A | * | 9/1996 | Nishi et al. ............... 355/30 |
| 6,191,849 B1 | * | 2/2001 | Maeshima et al. ......... 356/237.1 |
| 6,392,738 B1 | * | 5/2002 | van de Pasch et al. ......... 355/30 |
| 6,479,832 B1 | * | 11/2002 | Naraki et al. ............. 250/559.3 |
| 6,532,065 B1 | | 3/2003 | Grimme et al. |
| 2004/0239905 A1 | * | 12/2004 | Van Rhee et al. ............ 355/55 |
| 2005/0061995 A1 | * | 3/2005 | Vink et al. ............... 250/492.1 |
| 2006/0092393 A1 | | 5/2006 | Harned et al. |
| 2006/0139629 A1 | * | 6/2006 | Ohshima et al. .......... 356/237.2 |
| 2007/0035714 A1 | | 2/2007 | Galburt |

FOREIGN PATENT DOCUMENTS

| | | |
|---|---|---|
| JP | 1-212338 | 8/1989 |
| JP | 07-086131 | 3/1995 |
| JP | 07-128032 | 5/1995 |
| JP | 2006-128699 | 5/2006 |
| JP | 2007-049165 | 2/2007 |

OTHER PUBLICATIONS

Japanese Office Action mailed Mar. 6, 2012 in corresponding Japanese Patent Application No. 2010-532669.

* cited by examiner

LITHOGRAPHIC APPARATUS AND METHOD

CROSS-REFERENCE TO RELATED APPLICATIONS

This is the U.S. National Stage of PCT/IB2008/002977, filed Nov. 3, 2008, which in turn claims priority to U.S. Provisional Application No. 60/996,279, filed Nov. 8, 2007, the entire contents of both applications are incorporated herein by reference in their entireties.

FIELD

The present invention relates to a lithographic apparatus and method.

BACKGROUND

A lithographic apparatus is a machine that applies a desired pattern onto a target portion of a substrate. Lithographic apparatus can be used, for example, in the manufacture of integrated circuits (ICs). In that circumstance, a patterning device, which is alternatively referred to as a mask or a reticle, may be used to generate a circuit pattern corresponding to an individual layer of the IC, and this pattern can be imaged onto a target portion (e.g. including part of, one or several dies) on a substrate (e.g. a silicon wafer) that has a layer of radiation-sensitive material (resist). In general, a single substrate will contain a network of adjacent target portions that are successively exposed. Known lithographic apparatus include so-called steppers, in which each target portion is irradiated by exposing an entire pattern onto the target portion in one go, and so-called scanners, in which each target portion is irradiated by scanning the pattern through the beam in a given direction (the "scanning"-direction) while synchronously scanning the substrate parallel or anti-parallel to this direction.

Lithography was traditionally undertaken on rigid substrates and/or wafers. While this still continues, in more recent years other applications for lithography have become more popular. For example, recently, applications such as flexible electronics and flexible displays have caused a worldwide research effort on the use of lithographic processes (especially batch processes) on flexible substrates. The fact that optical lithography (and imprint lithography) is a mature technology on rigid substrates makes it a good choice for use in applications which use flexible substrates. However, the translation of optical lithography (and imprint lithography) on rigid substrates to optical lithography (and imprint lithography) on flexible substrates is not straightforward. It may be difficult when trying to use optical lithography (and imprint lithography) to apply patterns to flexible substrates due to the flexible nature of the substrates. Being flexible, the substrates are more susceptible to out-of-plane deformation due to, for example: contamination between the flexible substrate and a surface on which the flexible substrate lies; the flatness of the surface on which the flexible substrate lies; or the flatness of an intermediate layer located in between the flexible substrate and a support structure, for example a glue layer.

It is desirable to provide, for example, an apparatus and method which obviates or mitigates one or more of the problems of the prior art, whether identified herein or elsewhere.

SUMMARY

According to an aspect of the present invention, there is provided a method of obtaining information indicative of the topography of a surface of a flexible substrate, the method including: directing a beam of radiation at the surface of the flexible substrate; and detecting changes in the intensity distribution, or angle of reflection, of the beam of radiation after the beam of radiation has been reflected from the surface of the substrate to obtain information indicative of the topography of the surface of the flexible substrate.

According to an aspect of the present invention, there is provided an apparatus arranged to obtain information indicative of the topography of a flexible substrate, the apparatus including: an electromagnetic radiation source arranged to provide a beam of radiation in the direction of a surface of the flexible substrate; and an electromagnetic radiation detector arranged to detect the intensity distribution, or angle of reflection, of at least a part of the beam of radiation after it has been reflected from the surface of the substrate.

According to another aspect of the present invention, there is provided a method of applying a pattern to a substrate, the method including: using information indicative of the topography of the substrate to define a plurality of grid sections, each grid section being associated with an area of the substrate to which the pattern is to be applied, and each grid section having associated with it: a set of exposure conditions which are used to define a depth of focus for that grid section, a peak-to-valley variation in the topography of the area of the substrate associated with a grid section being encompassed by the depth of focus for that grid section; or a substrate position or orientation which is used to control the position or orientation of the substrate such that the area of the substrate to which the pattern is to be applied is within a given depth of focus; the method further including applying a pattern to the substrate in accordance with the exposure conditions, or substrate positions or orientations, defined by the grid sections.

According to an aspect of the present invention, there is provided a controller for use in or with a lithographic apparatus, the controller being arranged to take into account a plurality of grid sections which have been defined using information indicative of the topography of the substrate, each grid section being associated with an area of the substrate to which the pattern is to be applied, and each grid section being associated with: a set of exposure conditions which are used to define a depth of focus for that grid section, a peak-to-valley variation in the topography of the area of the substrate associated with a grid section being encompassed by the depth of focus for that grid section; or a substrate position or orientation which is used to control the position or orientation of the substrate such that the area of the substrate to which the pattern is to be applied is within a given depth of focus; the controller being arranged to control the apparatus for applying a pattern to the substrate in accordance with the exposure conditions, or substrate positions or orientations defined by the grid sections

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION

Figure 1:
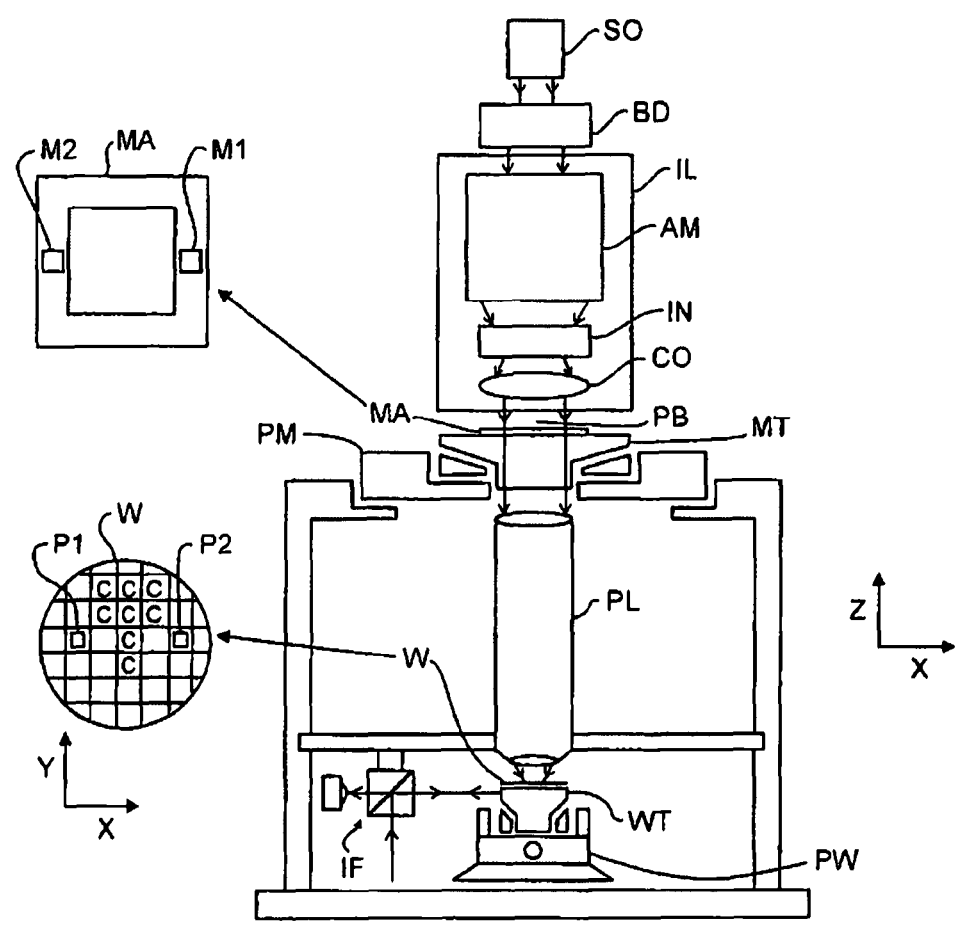
FIG. 1 depicts an example of a lithographic apparatus in accordance with an embodiment of the invention.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, liquid-crystal displays (LCDs), thin-film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist) or a metrology or inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

The terms "radiation" and "beam" used herein encompass all types of electromagnetic radiation, including ultraviolet (UV) radiation (e.g. having a wavelength of 365, 248, 193, 157 or 126 nm) and extreme ultra-violet (EUV) radiation (e.g. having a wavelength in the range of 5-20 nm), as well as particle beams, such as ion beams or electron beams.

The term "patterning device" used herein should be broadly interpreted as referring to a device that can be used to impart a radiation beam with a pattern in its cross-section such as to create a pattern in a target portion of the substrate. It should be noted that the pattern imparted to the radiation beam may not exactly correspond to the desired pattern in the target portion of the substrate. Generally, the pattern imparted to the radiation beam will correspond to a particular functional layer in a device being created in the target portion, such as an integrated circuit.

A patterning device may be transmissive or reflective. Examples of patterning device include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions; in this manner, the reflected beam is patterned.

The support structure holds the patterning device. It holds the patterning device in a way depending on the orientation of the patterning device, the design of the lithographic apparatus, and other conditions, such as for example whether or not the patterning device is held in a vacuum environment. The support can use mechanical clamping, vacuum, or other clamping techniques, for example electrostatic clamping under vacuum conditions. The support structure may be a frame or a table, for example, which may be fixed or movable as required and which may ensure that the patterning device is at a desired position, for example with respect to the projection system. Any use of the terms "reticle" or "mask" herein may be considered synonymous with the more general term "patterning device".

The term "projection system" used herein should be broadly interpreted as encompassing various types of projection system, including refractive optical systems, reflective optical systems, and catadioptric optical systems, as appropriate for example for the exposure radiation being used, or for other factors such as the use of an immersion fluid or the use of a vacuum. Any use of the term "projection lens" herein may be considered as synonymous with the more general term "projection system".

The illumination system may also encompass various types of optical components, including refractive, reflective, and catadioptric optical components for directing, shaping, or controlling the beam of radiation, and such components may also be referred to below, collectively or singularly, as a "lens".

The lithographic apparatus may be of a type having two (dual stage) or more substrate tables (and/or two or more support structures). In such "multiple stage" machines the additional tables may be used in parallel, or preparatory steps may be carried out on one or more tables while one or more other tables are being used for exposure.

The lithographic apparatus may also be of a type wherein the substrate is immersed in a liquid having a relatively high refractive index, e.g. water, so as to fill a space between the final element of the projection system and the substrate. Immersion techniques are well known in the art for increasing the numerical aperture of projection systems.

FIG. 1 schematically depicts an example of a lithographic apparatus in accordance with an embodiment of the invention. The apparatus includes an illumination system (illuminator) IL to condition a beam PB of radiation (e.g. UV radiation or EUV radiation); a support structure or patterning device support (e.g. mask table) MT to support a patterning device (e.g. a mask) MA and connected to first positioning device PM to accurately position the patterning device with respect to item PL; a substrate table (e.g. a wafer table) WT configured to hold a substrate (e.g. a flexible substrate or wafer) W and connected to second positioning device PW configured to accurately position the substrate with respect to item PL; and a projection system (e.g. a refractive projection lens) PL configured to image a pattern imparted to the radiation beam PB by patterning device MA onto a target portion C (e.g. including one or more dies) of the substrate W.

As here depicted, the apparatus is of a transmissive type (e.g. employing a transmissive mask). Alternatively, the apparatus may be of a reflective type (e.g. employing a programmable mirror array of a type as referred to above).

The illuminator IL receives a beam of radiation from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including for example suitable directing mirrors and/or a beam expander. In other cases the source may be integral part of the apparatus, for example when the source is a mercury lamp. The source SO and the illuminator IL, together with the beam delivery system BD if required, may be referred to as a radiation system.

The illuminator IL may include an adjuster AM configured to adjust the angular intensity distribution of the beam. Generally, at least the outer and/or inner radial extent (commonly referred to as σ-outer and σ-inner, respectively) of the intensity distribution in a pupil plane of the illuminator can be adjusted. In addition, the illuminator IL generally includes various other components, such as an integrator IN and a condenser CO. The illuminator provides a conditioned beam of radiation PB, having a desired uniformity and intensity distribution in its cross-section.

The radiation beam PB is incident on the patterning device (e.g. mask) MA, which is held on the support structure MT. Having traversed the patterning device MA, the beam PB passes through the projection system PL, which focuses the beam onto a target portion C of the substrate W. With the aid of the second positioning device PW and position sensor IF (e.g. an interferometric device), the substrate table WT can be moved accurately, e.g. so as to position different target portions C in the path of the beam PB. Similarly, the first positioning device PM and another position sensor (which is not explicitly depicted in FIG. 1) can be used to accurately position the patterning device MA with respect to the path of the beam PB, e.g. after mechanical retrieval from a mask library, or during a scan. In general, movement of the object tables MT and WT will be realized with the aid of a long-stroke module (coarse positioning) and a short-stroke module (fine positioning), which form part of the positioning device PM and PW. However, in the case of a stepper (as opposed to a scanner) the support structure MT may be connected to a short stroke actuator only, or may be fixed. Patterning device MA and substrate W may be aligned using patterning device alignment marks M1, M2 and substrate alignment marks P1, P2.

The depicted apparatus can be used in the following preferred modes:

1. In step mode, the support structure MT and the substrate table WT are kept essentially stationary, while an entire pattern imparted to the beam PB is projected onto a target portion C in one go (i.e. a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the support structure MT and the substrate table WT are scanned synchronously while a pattern imparted to the beam PB is projected onto a target portion C (i.e. a single dynamic exposure). The velocity and direction of the substrate table WT relative to the support structure MT is determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the support structure MT is kept essentially stationary holding a programmable patterning device, and the substrate table WT is moved or scanned while a pattern imparted to the beam PB is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2A:
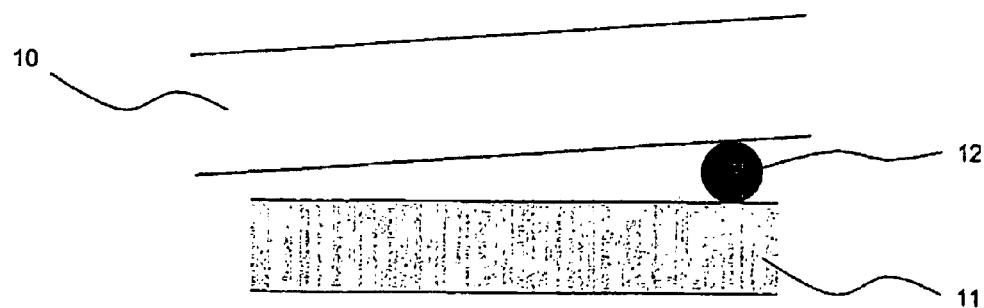
FIGS. 2a and 2b depict the effects of contamination on the flatness of a rigid substrate.
Figure 2B:
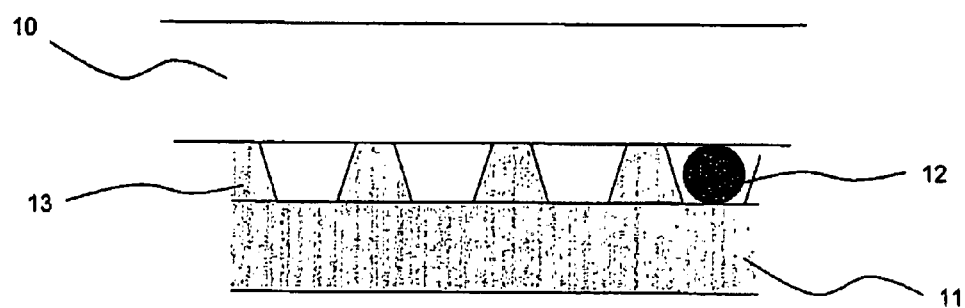

FIGS. 2a and 2b depict a rigid substrate 10 carried by a substrate table 11 (for example, the substrate table WT of FIG. 1). The substrate 10 may be, for example, a silicon wafer. Contamination 12 in the form of a particle or the like is located in-between the rigid substrate 10 and the substrate table 11.

In FIG. 2a, it can be seen that the substrate table 11 is flat. It can be seen that contamination 12 causes the rigid substrate 10 to lie at an angle with respect to the substrate table 11. In other words, the rigid substrate 10 does not lie flat on the substrate table 11 because of the contamination 12 located between the rigid substrate 10 and substrate table 11. Because the contamination 12 is usually relatively small in size (for example, of the order of micrometers and below, due to the controlled environment in which lithography usually takes place), the angle at which the rigid substrate 10 is inclined with respect to the substrate table 11 is small. It can be seen that the rigid substrate 10 does not bend around the contamination 12. In other words, the rigid substrate 10 still provides a flat surface on which a pattern may be applied, even if this flat surface lies at an angle to the substrate table 11. Although the flat surface lies at an angle to the substrate table 11, the angle can nevertheless be taken into account when applying patterns to the substrate 10 since all areas of the substrate will lie at only a small and common angle to the substrate table 11. In other words, the effect of the contamination 12 on the flatness of a rigid substrate 10 is a global effect, and can therefore more easily be taken into account and compensated for. A rigid substrate 10 is also capable of compressing or squeezing contamination 12 located between the substrate 10 and the substrate table 11, causing the substrate 10 to lie flatter on the substrate table 11.

FIG. 2b illustrates another example, where the substrate table 11 has been provided with an array of burls 13. One of the functions of the burls 13 is to allow contamination 12 to fall in-between the burls 13. Because the contamination 12 can fall between the burls 13, the rigid substrate 10 can still lie flat with respect to the substrate table 11, since the substrate 10 will lie on top of the burls 13. Therefore, in this embodiment, the substrate 10 can lie flat with respect to the substrate table 11 despite the presence of contamination 12 between the substrate table 11 and the rigid substrate 10. Referring to both FIGS. 2a and 2b, it can be seen that when rigid substrates 10 are used in lithography, either the contamination 12 does not have much of an effect on the flatness of the surface of the substrate 10 on to which patterns are to be applied, or the effect which the contamination 12 has on the flatness of the rigid substrate 10 with respect to the substrate table 11 can be diminished by the use of a substrate table 11 provided with an array of burls 13. This is in stark contrast to the situation where a flexible substrate is used.

Figure 3:
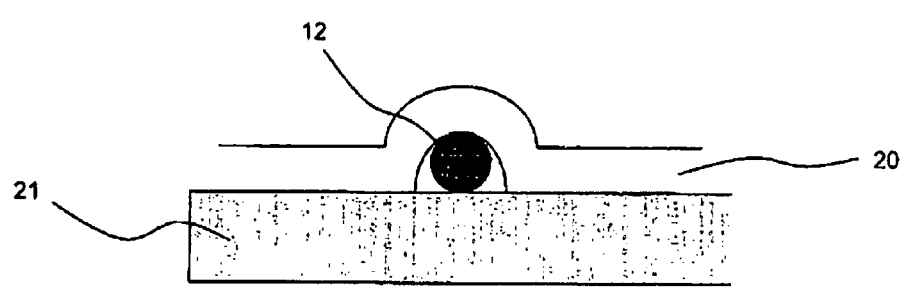
FIG. 3 depicts the effect of contamination on the flatness of a flexible substrate.

FIG. 3 depicts a flexible substrate 20. While the flexible substrate 20 could be held in place directly on a substrate table (for example the substrate table WT of FIG. 1), in practice it is more likely that the flexible substrate 20 will be attached to a supporting structure to give the flexible substrate 20 some rigidity when it is processed (e.g. exposed to radiation, cleaned, developed, etc). FIG. 3 therefore depicts the flexible substrate 20 attached to such a supporting structure 21. The supporting structure 21 may be a rigid substrate, such as that shown in FIG. 2a. The flexible substrate 20 may be attached to the supporting structure 21 using, for example, and intermediate layer including glue.

It can be seen that contamination 12 lies between the flexible substrate 20 and the supporting structure 21. Because the flexible substrate 20 is not rigid, and is flexible, the flatness of the flexible substrate 20 is greatly affected by the presence of the contamination 12. The thickness of the flexible substrate (which may be, for example, between zero and two hundred microns) may make it even more sensitive to contamination. It can be seen that the flexible substrate 20 may be flexible enough to take the general shape of the contamination 12 at the point where the contamination 12 is present. It will be appreciated that it is much more difficult to take into account non-uniformities in the flatness of a substrate when the non-uniformities are not smooth and gradual (e.g. global), as is generally the case with rigid substrates, but sharp and quickly varying (e.g. local), as is generally the case with flexible substrates. It may be difficult to take into account the non-uniformities in the flatness of the flexible substrate 20 (or, in other words, variations in the topography of the flexible substrate 20) when applying patterns to it, for example, by using imprint or optical lithography. The use of a substrate table (or other support structure) provided with an array of burls would not reduce or eliminate these difficulties, since the flexible substrate would take the shape of the burls, and sag in between spaces between burls, thereby creating a non-uniform surface.

In some applications, non-uniformities in the flatness of the flexible substrate 20 may not be that significant since the resolution of patterns applied to the flexible substrate 20 may be much lower than the dimensions of the non-uniformities. However, in recent years a trend towards smaller feature sizes has developed which means that such non-uniformities in flexible substrate 20 have become more of a problem. For example, whereas patterns having micron-sized features have previously been applied to flexible substrates, recent trends suggest that sub-micron sized features may soon be used (for example, nanometer sized features).

As a consequence of recent trends, it has become more desirable in recent years to investigate the topography (or in other words flatness) of flexible substrates before patterns are applied to them. Such investigations are undertaken to identify the locations and severity of non-uniformities in the flatness of the flexible substrates (in other words, to obtain information indicative of the topography of the substrate). Such non-uniformities can either be avoided during patterning of the flexible substrate, or the patterning techniques can be modified to take into account the non-uniformities. An example of an investigative method which may be used to investigate the topography of a flexible substrate involves interferometry. However, interferometry is considered to be an inaccurate method for determining the topography of a flexible substrate. This is because in many cases the flexible substrate is transparent (for example, a transparent plastic material). The transparent nature of the flexible substrate makes it difficult to determine the topography of its surface using interferometry. This is because some of the radiation used in interferometry to determine the topography of the surface of the flexible substrate may pass into the flexible substrate itself, and become scattered, reflected or refracted from different parts of the substrate. This makes it difficult to determine whether a detected signal has come from the surface of the substrate. It is therefore desirable to provide an improved apparatus and method for investigating the topography of a flexible substrate.

Figure 4:
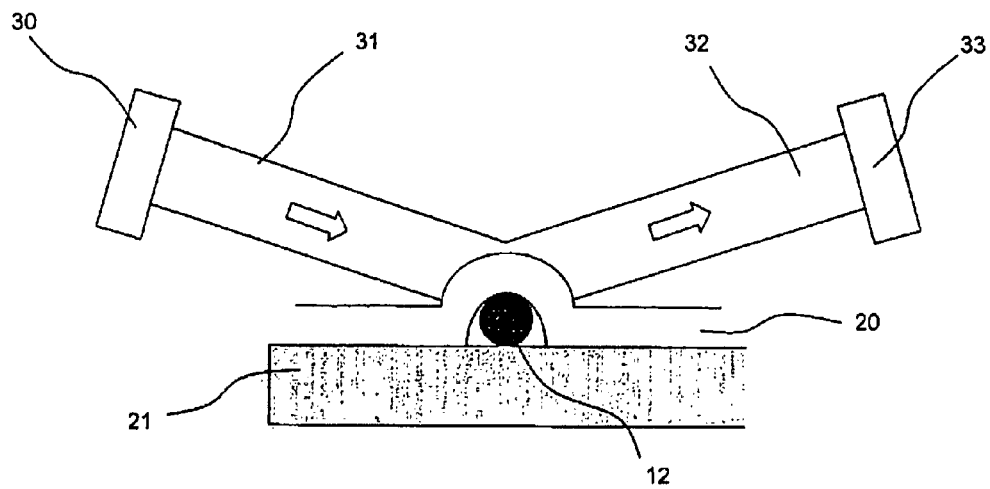
FIG. 4 depicts an apparatus and method for obtaining information indicative of the topography of a surface of a flexible substrate in accordance with an embodiment of the present invention.

FIG. 4 depicts an apparatus in accordance with an embodiment of the present invention. The apparatus is shown in conjunction with the supporting structure 21, contamination 12, and flexible substrate 20 shown in and described with reference to FIG. 3. Referring back to FIG. 4, an electromagnetic radiation source 30 is depicted. The radiation source 30 is shown emitting a beam of radiation 31 towards the flexible substrate 20. The incoming beam of radiation 31 is reflected by the surface on the flexible substrate 20, which results in a reflected beam of radiation 32. The reflected beam of radiation 32 is detected by an electromagnetic radiation detector 33. The angle of incidence of the incoming radiation 31 with respect to the flexible substrate 20 is high (i.e. the angle of the radiation when measured from a normal to the substrate's 20 surface is high), such that radiation penetrating beneath the surface of the flexible substrate 20 is reduced or eliminated. The angle of incidence of the beam of radiation 31 (measured from a normal to the substrate's 20 surface) may be selected to be greater than or equal to the critical angle of the flexible substrate 20 to reduce or eliminate the amount of radiation entering the substrate 20. As is known in the art, the critical angle of a material is proportional to the refractive index of that material.

Information indicative of the topography of the surface of the flexible substrate 20 can be determined by determining how the incoming beam of radiation 31 is affected by the surface of the flexible substrate 20. In other words, information indicative of the topography of the surface of the flexible substrate 20 can be determined by monitoring the beam of radiation 32 reflected from that surface.

Figure 5:
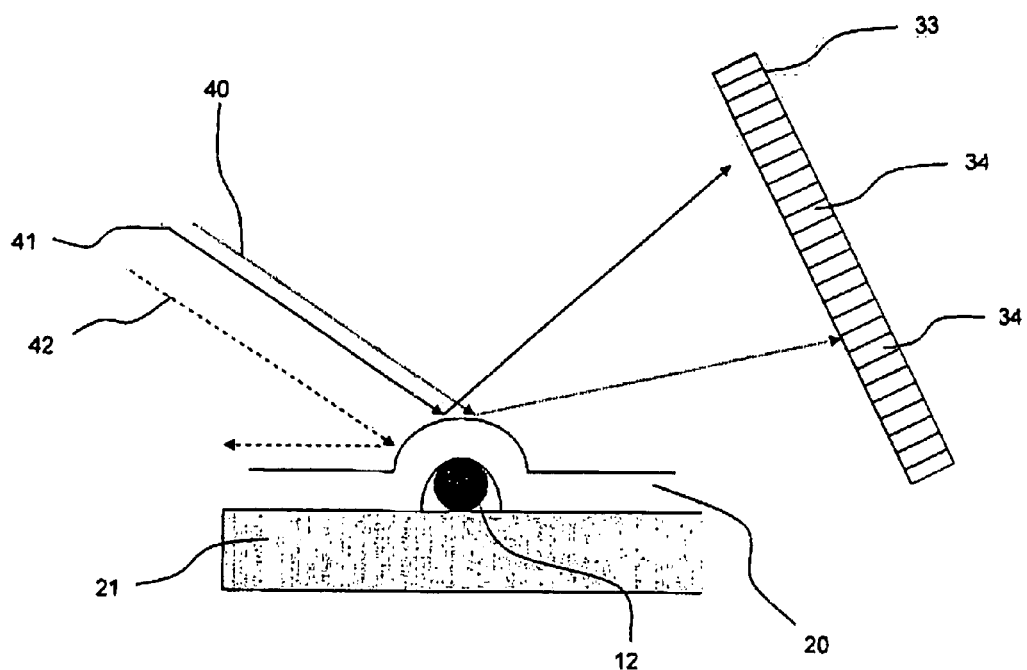
FIG. 5 depicts operating principles of the apparatus and method depicted in FIG. 4.

FIG. 5 shows how information indicative of the topography of the surface of the flexible substrate 20 may be obtained using the apparatus of FIG. 4. It will be appreciated that FIG. 5 schematically depicts the effect on a radiation beam of a change in topography (e.g. a non-uniformity) of the surface of the flexible substrate 20. The exact nature of the effects of such a change in topography may, in reality, be slightly different and/or more or less complicated than as depicted in FIG. 5.

FIG. 5 depicts three exemplary portions of the incoming radiation beam 31 shown in FIG. 4. FIG. 5 shows a first portion 40, a second portion 41, and a third portion 42 all directed at slightly different parts of the surface of the flexible substrate 20. It can be seen that the first portion 40 is directed toward and incident upon an uppermost surface of a non-uniformity in the region of contamination 12. The upper-most surface is relatively flat, meaning that the first portion 40 of the radiation beam is reflected at a relatively high angle towards the detector 33 (when measured from the normal to a flat part of the substrate's surface). The second portion 41 of the radiation beam is also directed towards and incident upon an upper-most surface of the non-uniformity in the region of the contamination 12. However, the second portion 41 is incident upon a slightly different part of the non-uniformity to the first portion 40. The effect of this is that the angle at which the second portion 41 is reflected from the non-uniformity is less than the angle at which the first portion 40 is reflected from the non-uniformity (when measured from the normal to a flat part of the substrate's surface). It can be seen that the second portion 41 of the radiation beam will therefore be reflected toward a different part of the detector 33. The third portion 42 of the radiation beam is directed towards a lower-most surface of the non-uniformity in the region of the contamination 12. It can be seen that the part of the surface which the third-portion 42 is incident upon is angled such that the third portion 42 of the radiation beam is reflected away from the detector 33, and is thus not detected by the detector 33.

The detector 33 may be provided with or include a one or two-dimensional photo diode array which includes an array of photo diodes 34. Alternatively the detector 33 may be provided with or include any detection means for detecting radiation incident on different parts of the detector, either in one or two dimensions. One dimensional detection may be suitable or preferred if the radiation beam 31 directed at the surface of the flexible substrate 20 has a narrow width (e.g. into and/or out of the plane of the Figure). If the beam has a substantial width, for example a circular cross section, two-dimensional scattering from the surface of the substrate is more likely, and a two-dimensional detector may then be suitable.

It will be appreciated from FIG. 5 and its description that various features of a change in the topography (e.g. a non-uniformity) of the surface of the flexible substrate 20 can be determined. For example, if there is no change in the topography of the surface of the flexible substrate 20 (in other words, there is no non-uniformity), the radiation beam reflected from the surface of the flexible substrate 20 will be uniform and un-changing, when, for example, there is relative movement between the radiation beam 31 and the flexible substrate 20. In another example, the severity of the non-uniformity (e.g. an approximation of its height or width) may be obtained by determining the angular intensity distribution of the radiation beam reflected from the surface of the non-uniformity. For example, it can be seen in FIG. 5 that if the non-uniformity is convex the reflected radiation beam 32 will spread out. The degree to which the reflected radiation beam 32 spreads may be determined by monitoring which parts of the detector 33 (e.g. which photodiodes 34) detect a part of the reflected radiation beam, or what intensity of radiation these parts detect. Conversely, if the non-uniformity is concave, at least a part of the reflected radiation beam 32 may become more focused, resulting in a detectable change in the angular intensity distribution of the radiation beam detected by the detector 33. In another example, a change in the total (e.g. integrated) intensity of the reflected radiation beam 32 may also be used to determine whether a non-uniformity has been encountered. It can be seen that, for example, a portion 42 of the radiation beam may be reflected away from the detector, meaning that the intensity of the reflected beam is less than the intensity of the incident beam. Changes in the intensity distribution or angle of reflection or both of the beam of radiation after the beam of radiation has been reflected from the surface of the substrate may be detected to obtain information indicative of the topography of the surface.

If the radiation beam used is small enough, it may be that movement of the reflected radiation beam (and not parts of the radiation beam) may be used to obtain information indicative of the topography of the substrate. For example, FIG. 5 shows a first portion 40, a second portion 41, and a third portion 42 of a radiation beam all directed at slightly different parts of the surface of the flexible substrate 20. However, this Figure could similarly represent a single, smaller, radiation beam being moved relative to the substrate, each 'portion' then representing different incident positions and reflected angles of the beam. The extent and rate of movement of the reflected beam may give an indication of the height or size of the contamination causing the change in the topography or, more generally speaking an indication in the height and size of the change (or non-uniformity) in the topography.

Level sensors are used in lithography to determine the topography of rigid substrates. According to an embodiment of the present invention, a level sensor may be used to obtain information indicative of the topography of a surface of a flexible substrate. Since level sensors are known in the art, they will not be described in any more detail here.

In FIGS. 4 and 5, a radiation beam is shown as being directed towards a non-uniformity in the surface of a flexible substrate. In practice, a radiation beam may be scanned across the substrate to determine information indicative of the topography of all or part of a surface of the substrate. The substrate may, instead, be scanned or moved relative to the radiation beam. In FIGS. 4 and 5, a single beam is shown as being directed towards the flexible substrate. It will be appreciated that this is not essential, and more than one beam may be used. For example, more than one beam and/or more than one detector may be used. For example, one, two, three, four or more beams of radiation may be directed towards the substrate at any one time. Multiple beams of radiation may be directed at the same point on a substrate from different (for example orthogonal or opposite) directions. More information regarding the topography of the substrate, and in particular the topography of non-uniform part of the substrate may be obtainable by using a plurality of beams. In another example, information regarding the topography of the substrate may be obtained more quickly by using more than one radiation beam. Alternatively, a single beam can be scanned across the substrate, or the substrate scanned relative to the radiation beam, in a number of different directions, orientations, configurations, etc., instead of using a plurality of radiation beams.

It is to be appreciated that the wavelength of radiation which forms the radiation beam, and/or the diameter of the radiation beam, may be constant or varied. Varying the wavelength and/or diameter may increase the sensitivity of any results obtained. For example, if the diameter of the radiation beam is similar to that of the dimensions of non-uniformities on the substrate, more detail about the shape of the non-uniformity may be forthcoming. For instance, if the diameter of the radiation beam greatly exceeds the dimensions of the non-uniformity, it may be difficult to detect changes in the reflected radiation beam caused by the non-uniformity. Conversely, if the diameter of the radiation beam is much smaller than the size of non-uniformities on the surface of the substrate, it may also be difficult to detect any changes in the reflection of radiation from the substrate. This is because these changes are likely to be quite severe, and a reflected beam may be reflected at one of a range of angles, possibly not detectable by a detector fixed in one location. If the diameter of the radiation beam is similar to the size of the non-uniformity, a balance is struck where at least some of the radiation will be reflected towards the detector, which may be used to determine properties of the non-uniformity. The diameter of the radiation beam may therefore be any appropriate value, but may be, for example between one micrometer and one hundred micrometers in diameter, or between one micrometer and ten micrometers in diameter. One or more beams having different diameters may be used simultaneously or successively in order to, for example, obtain coarser or finer topography information. For instance, a beam with a larger diameter may be used to obtain coarse topography information, and if sufficient variation in the topography is found then a beam with a smaller diameter may be used to obtain finer (e.g. higher resolution) information. The smaller diameter beam may be used to obtain finer information of certain areas of the substrate, for example those areas found to have the greatest topography variation using the larger diameter beam.

Preferably, the wavelength of radiation which forms the radiation beam is such that the radiation beam does not affect, for example, a resist layer provided on the flexible substrate. For example, the wavelength of the radiation beam may be in the red region of the visible part of the electromagnetic spectrum, or in the infra-red region of the electromagnetic spectrum.

The angle at which the radiation beam is directed at the substrate (as measured from a normal of the substrate) should ideally be such that the amount of radiation which passes into the substrate is minimized. For example, the angle of incidence could be equal to or greater than the critical angle for the substrate. The angle of incidence could be between forty five degrees and eighty degrees (as measured from a normal of the substrate).

The angle at which the radiation beam is directed at the flexible substrate, the wavelength of the radiation beam and the diameter of the radiation beam can all be controlled by controlling properties of the radiation source (e.g. its position, orientation, output wavelength, slit width, aperture diameter, etc.), or equipment used in conjunction with the radiation source (e.g. mirrors, lenses, etc.).

In the embodiments described above, a flexible substrate has been discussed. A flexible substrate may be formed from any material, for example a metal or a plastic. The flexible substrate may be a flexible transparent or opaque plastic sheet, or may be a metallic foil, for example. It is to be appreciated that the methods and apparatus described above may be used for any flexible substrate.

Figure 6:
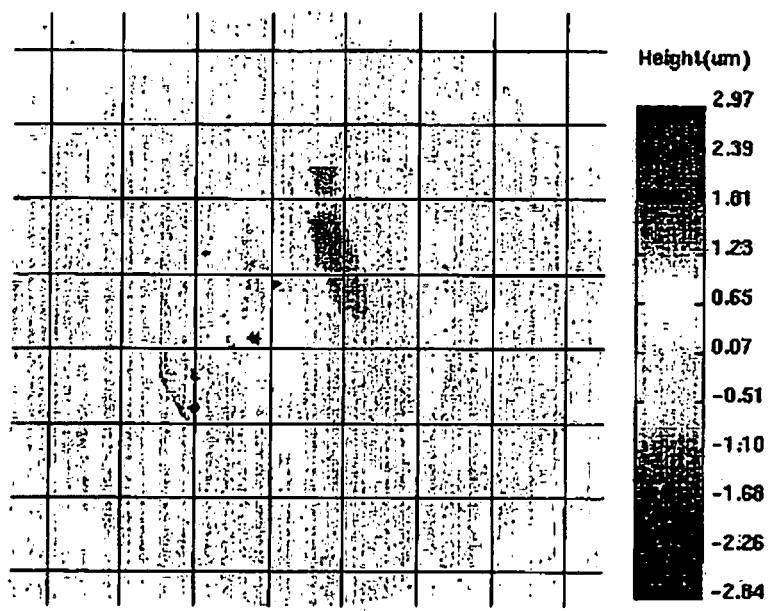
FIG. 6 depicts the non-uniformity in the flatness of a flexible substrate.

FIG. 6 depicts topographical results for a flexible substrate obtained using the methods and apparatus described above. The results are presented in grayscale, where an increased darkness of the shaded areas indicates a greater departure from an average (e.g. flat) surface level. It can be seen that there are a plurality of individual dark regions, where, for example, contamination may be present between the flexible substrate and a support structure on which the substrate is held, or where there are variations in thickness of an intermediate laminate or glue layer between the substrate and the support structure. There are also other regions which are not flat, but which are larger in size than those typical of particle contamination. These regions may indicate that the substrate itself is thicker or thinner at these points, or that the surface upon which the substrate is placed is thicker or thinner at these points. It can also be seen that there are regions where the substrate is flat. In summary, it can be seen that for a flexible substrate the presence of gradual and localized non-uniformities is confirmed. Furthermore, it can be seen that these non-uniformities vary in size and extent. Because these non-uniformities in (or, in other words, variations in the topography of) the flexible substrate vary across the substrate, it is difficult to apply uniform patterns to the substrate without making some corrections in the conditions used to apply the patterns. If these corrections are not made, patterns applied to the substrate may be defective.

The method according to an embodiment of the present invention described above can be undertaken in a lithographic apparatus or external to a lithographic apparatus (e.g. in a standalone apparatus). Similarly, the apparatus described above can be part of a lithographic apparatus, or a part of another apparatus, or a standalone piece of apparatus. The apparatus according to an embodiment of the present invention may be housed in a chamber which may be arranged to reduce the amount of contamination contained within the chamber. For example, the chamber may be at a positive or negative pressure with respect to the environment external to the chamber. The chamber may be evacuated.

Figure 7:
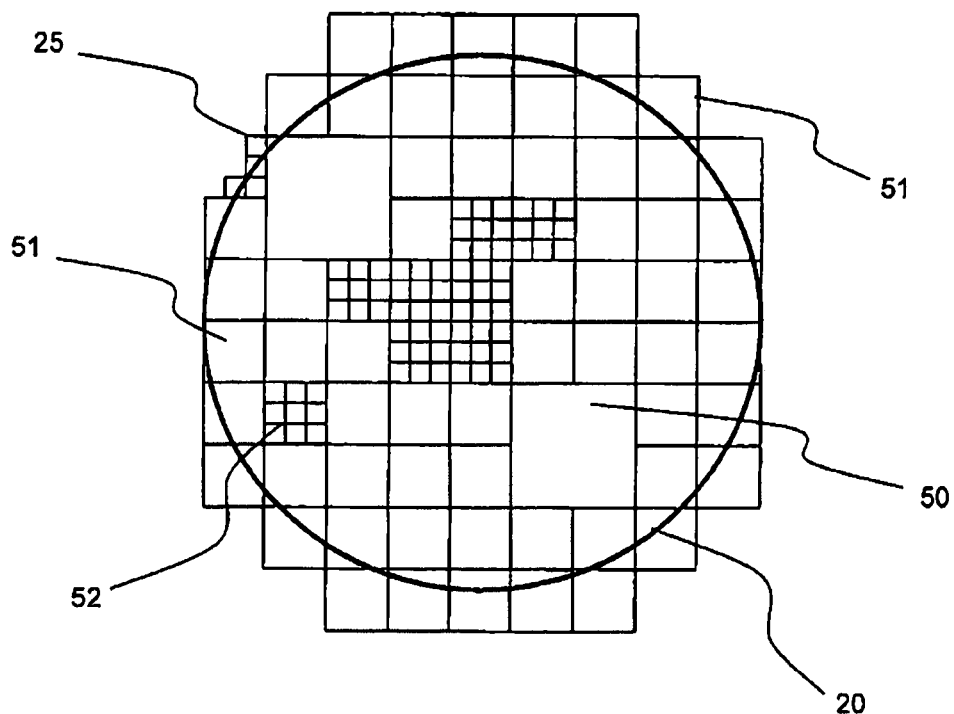
FIG. 7 depicts a lithographic method in accordance with another embodiment of the present invention, where the flatness of a substrate to which a pattern is to be applied is taken into account during the application of patterns.

FIG. 7 depicts an embodiment of the present invention. A flexible substrate 20 is shown in plan view. As shown in and described with reference to FIGS. 3-6, the flexible substrate 20 is not flat, and instead includes many non-uniformities (in other words, variations) in its topography. Ideally, the flatness of the flexible substrate 20 needs to be optimized to achieve sub-micron patterning of the flexible substrate 20. However, and as described above, it may be difficult to ensure that the flexible substrate 20 is flat due to contamination and processing conditions which may introduce non-uniformities in the flatness of the flexible substrate 20. When the topography of the surface of the flexible substrate 20 varies (i.e. when the surface of the flexible substrate 20 is not flat) the depth of focus may be locally sacrificed on and around the variation (e.g. non-uniformity), leading to deteriorated or defective patterns. In other words, the depth of the focus may be sacrificed such that the patterns applied to the substrate are not sufficiently sharp. For example, the patterns may have blurred edges, and these edges may become too blurred if the non-uniformities in the surface of the substrate are beyond certain limits, for example are too deep or too high. To apply high quality, uniform patterns across the surface of the substrate, it is preferable to try to ensure that that the surface of the substrate is within an acceptable depth of focus range during the application of patterns to the substrate.

In order to ensure that non-uniformities in the surface of the substrate do not cause patterns to be defective, while at the same time not sacrificing the feature size (in other words, critical dimension) of patterns applied to the substrate, as well as throughput time, an adaptive grid refinement method according to an embodiment of the present invention is used to project patterns onto the surface of the substrate. Conventional optical lithography equipment may be controlled to implement this method.

The method involves using information indicative of the topography of the substrate to define a number of grids which are associated with exposure conditions to be used to apply patterns to the flexible substrate 20. Information indicative of the topography of the substrate may be obtained using the method and apparatus described above in relation to FIGS. 3 to 6.

The method may involve defining a coarse grid. Areas of the substrate that satisfy desired topography conditions (in other words, are a desired flatness have a certain peak-to-valley variation in their topography) may be used to define one or more parts of this grid. Exposure conditions (for example, magnification, focus, power, numerical aperture, etc) are defined for this coarse grid, such that the exposure conditions result in a depth of focus which encompasses the peak-to-valley variation in the topography of areas of the substrate which define the coarse grid. FIG. 7 illustrates sections of a coarse grid 50.

Next, a finer grid is defined for those locations on the substrate that do not satisfy the topography requirements of the coarse grid (in other words, have a flatness or peak-to-valley variation in their topography which is greater than that of the areas of the substrate defining the coarse grid 50). Exposure conditions (for example, magnification, focus, power, numerical aperture, etc) are defined for this finer grid, such that the exposure conditions result in a depth of focus which encompasses the peak-to-valley variation in the topography of areas of the substrate which define the finer grid. FIG. 7 shows examples of sections of this finer grid 51.

Finally, an additional and even finer grid may be defined to take into account very localized variations and/or sharply varying variations in the topography of the flexible substrate. Exposure conditions (for example, magnification, focus, power, numerical aperture, etc) are defined for this even finer grid, such that the exposure conditions result in a depth of focus which encompasses the peak-to-valley variation in the topography of areas of the substrate which define the even finer grid. Sections of this even finer grid 52 are also shown in FIG. 7.

The coarse grid sections 50, fine grid sections 51 and even finer grid sections 52 respectively form a coarse grid section set, a fine grid section set and even finer grid section set. Each set has a common set of exposure conditions associated with it.

As mentioned above, the depth of focus of the exposure conditions defined for each grid section should ideally encompass the maximum peak-to-valley variation in the topography of the surface of the substrate defined by that grid section. This means that, when the substrate is patterned using the conditions defined by each grid section, the applied patterns should have an acceptable image quality across the entire area of the flexible substrate. In practice, there is a depth of focus 'budget'. As well as the depth of focus needing to encompass the peak-to-valley variation in the topography of the surface of the substrate, it also needs to encompass process variations and deviations in the optics of the lithographic apparatus. Therefore, in order to take into account all of these factors, the depth of focus of the exposure conditions defined for each grid section should ideally be two to three times greater than the average (or maximum) peak-to-valley variation in the topography of the surface of the substrate defined by that grid section.

The exposure of the substrate using the conditions defined by the grid sections may lead to exposure conditions being changed as each adjacent substrate area which defines a different grid section is exposed to radiation. Alternatively, the substrate 50 may be exposed to radiation in sequential order of the size of the grids. For example, all of the substrate areas associated with coarse grid sections 50 could be exposed first, followed by the fine grid sections 51, followed finally by the even finer grid sections 52. In other words, substrate areas associated with grid sections of a first grid section set may be patterned before substrate areas associated with grid sections of a second grid section set, and so on. As is known in the art, optical stitching may be required between adjacent grid sections to ensure that there is little or no discontinuity in patterns which extend across borders of adjacent grid sections. Since optical stitching is known, it will not be described in anymore details here.

As mentioned above in relation to FIG. 7, an adaptive grid refinement method according to an embodiment of the present invention is used to project patterns onto the surface of the substrate. Conventional optical lithography equipment may be controlled to implement this method. In the above method, exposure conditions (for example, magnification, focus, power, numerical aperture, etc) are defined to ensure that in each grid section, or grid section set, the depth of focus encompasses the peak-to-valley variation in the topography of areas of the substrate which define the grid section, or grid section set. This is not the only way in which the grid method may be implemented. Instead, each grid section may have associated with it a substrate position or orientation which is then used to control the position or orientation of the substrate such that a surface of the substrate to which the pattern is to be applied is within a given depth of focus. For example, the substrate may be moved horizontally or vertically, rotated or tilted to ensure that the surface of the substrate to which the pattern is to be applied (for example, the area associated with or defined by the grid section or grid section set) is within a given depth of focus. The given depth of focus may be a standard or default depth of focus, or could be a depth of focus which varies between grid sections, as described above (i.e. a grid section may be associated with a set of exposure conditions and a substrate position or orientation). The method using substrate positions or orientations could be implemented by conventional optical lithography equipment, for example by controlling the position or orientation of a substrate table or holder which holds the substrate. All features described in and with reference to FIG. 7 are equally applicable to the method of controlling the position or orientation of the substrate. For example, the position or orientation of the substrate may change or be the same for adjacent grid section sets. Grid sections may be grouped into grid sections. Grid sections or section sets with the same or similar properties may be exposed consecutively. Coarse, fine and finer (etc.) grid sections may be defined.

The method described in relation to FIG. 7 is particularly applicable to the exposure to radiation of flexible substrates, since flexible substrates are particularly susceptible to non-uniformities in their flatness (or in other words, topography) as described in detail above. However, the method described in relation to FIG. 7 is also applicable to rigid substrates, where changes in the flatness (or in other words topography) of the rigid substrates are know to occur, even if these changes are not as severe as they are in the case of flexible substrates.

In FIG. 7, square grid sections have been shown. However, other shapes of grid section may be used. Preferably, these grid sections will tessellate (i.e. leave no gaps). The grid sections may be square in shape, rectangular in shape, triangular in shape, etc. However, square or rectangular grid sections will be preferred since they may be more easily implemented using conventional lithographic apparatuses, since such apparatuses apply patterns to substrates in square or rectangular step exposures, or scanned exposure which result in square or rectangular shaped exposed areas.

A controller may be provided which is arranged to control a lithographic apparatus to effect the grid method described above. For example, the controller may be configured to take into account information indicative of the topography (or in other words flatness) of the substrate, and may also be configured to control the depth of focus of the lithographic apparatus by controlling some or all parts of the apparatus to change the exposure conditions in order to take into account the topographic information. The controller may be configured to control some or all parts of the lithographic apparatus (e.g. those parts that control properties of the radiation beam, as discussed in relation to FIG. 1, above) to ensure that the exposure conditions (such as magnification, focus, power, numerical aperture, etc) are such that the depth of focus across the entire surface of the substrate is within acceptable limits. The controller may be a computer or the like, or software or code on a computer or the like. The controller may be a part of the lithographic apparatus, or may be in communication with the lithographic apparatus.

Alternatively or additionally, a controller may be provided which is arranged to control a lithographic apparatus to effect an alternative grid method described above. For example, the controller may be configured to take into account information indicative of the topography (or in other words flatness) of the substrate, and may also be configured to control the position or orientation of the substrate to ensure that an area of the substrate to which a pattern is to be applied (e.g. a grid section) is within a given depth of focus. The controller may be configured to control some or all parts of the lithographic apparatus, for example a substrate table or holder which holds the substrate in position. The controller may be a computer or the like, or software or code on a computer or the like. The controller may be a part of the lithographic apparatus, or may be in communication with the lithographic apparatus. The controller for controlling the exposure conditions mentioned above may the same as, or independent of, the controller for controlling the position and or orientation of the substrate.

In the above embodiments, non-uniformities in the flatness of a flexible substrate have been described as being caused by contamination. It will be appreciated that a non-uniformity may arise for any one of a number of reasons. For example, non-uniformities in the flatness of a flexible substrate may arise from a variation in a thickness of the flexible substrate itself, or warping due to process conditions such as moisture and temperature. Non-uniformities may also be introduced in the surface of the flexible substrate when the substrate is handled, for example by robot tools or the like, or by variations in thickness in an intermediate layer (e.g. glue) between the flexible substrate and a supporting structure (e.g. a rigid substrate). The thickness variations in the intermediate layer may be caused by different stresses, etc., in the intermediate layer.

In the above embodiments, the obtaining and use of information indicative of the topography of the surface of a substrate has been described. Such information may be actual values of the heights or depths of various parts of the substrate. Alternatively, the information may be changes in detected intensities of reflected beams, or the spreading or focusing of reflected beams, from which topographical information may be obtained. In general, information indicative of the topography of the surface of a substrate may be direct values, in that the information includes one or more values of actual spatial variations of the surface, or indirect values, in that the information includes one or more values which can be used to determine the topography of the surface.

The above methods and apparatuses have been described in relation to the application of patterns to a substrate. Such patterns may be used to form devices. The above methods and apparatuses according to embodiments of the present invention may therefore also be used in one or more process phases of the formation of such devices.

While specific embodiments of the invention have been described above, it will be appreciated that the invention may be practiced otherwise than as described. The description is not intended to limit the invention.

The invention claimed is:

1. A method of obtaining information indicative of the topography of a surface of a flexible substrate, the method comprising:
   directing a beam of radiation at the surface of the flexible substrate, the topography comprising a recess and/or protrusion of the surface;
   detecting angular or spatial changes in intensity distribution, or changes in angle of reflection, of the beam of radiation after the beam of radiation has been reflected from the surface of the substrate; and
   determining information indicative of the height relative to the surface, or size, of the topography of the surface of the flexible substrate from the extent and/or rate of change of the detected changes in intensity distribution or angle of reflection.

2. The method of claim 1, wherein the beam of radiation is directed at the surface of the flexible substrate at an angle which is equal to or greater than the critical angle of the flexible substrate.

3. The method of claim 1, wherein the beam of radiation has a diameter which is between about one micrometer and one hundred micrometers.

4. The method of claim 1, comprising undertaking the method using a beam of radiation having a first diameter, and then undertaking the method using a beam of radiation having a second diameter, the second diameter being smaller than the first diameter.

5. The method of claim 1, comprising relatively moving the beam of radiation and the substrate.

6. The method of claim 1, comprising directing a plurality of beams of radiation from different directions at a same location of the substrate.

7. The method of claim 1, wherein the directing of a beam of radiation at the surface of the flexible substrate, and the detection of the changes in the intensity distribution, or the angle of reflection, of the beam of radiation after the beam of radiation has been reflected from the surface of the substrate to obtain information indicative of the topography of the surface of the flexible substrate is undertaken using a level sensor.

8. The method of claim 1, wherein the flexible substrate comprises a metal foil or a plastic sheet.

9. The method of claim 1, comprising determining the information indicative of the height relative to the surface, or size, of the topography of the surface of the flexible substrate from the rate of change of the detected changes in intensity distribution or angle of reflection.

10. An apparatus arranged to obtain information indicative of the topography of a flexible substrate, the apparatus comprising:
   an electromagnetic radiation source arranged to provide a beam of radiation in a direction of a surface of the flexible substrate, the topography comprising a recess and/or protrusion of the surface;
   an electromagnetic radiation detector configured to detect angular or spatial changes in intensity distribution, or changes in angle of reflection, of at least a part of the beam of radiation after it has been reflected from the surface of the substrate; and
   a processing system configured to determine information indicative of the height relative to the surface, or size, of the topography of the surface of the flexible substrate from the extent and/or rate of change of the detected changes in intensity distribution or angle of reflection.

11. The apparatus of claim 10, wherein the beam of radiation is arranged to be directed at the surface of the flexible substrate at an angle which is equal to or greater than the critical angle of the flexible substrate.

12. The apparatus of claim 10, wherein the beam of radiation has a diameter which is between about one micrometer and about one hundred micrometers.

13. The apparatus of claim 10, wherein the substrate is moveable relative to the radiation beam.

14. The apparatus of claim 10, wherein the radiation source is arranged to provide a plurality of beams of radiation, each beam being arranged to be directed at a same location of the surface of the substrate from different directions.

15. A method of applying a pattern to a substrate, the method comprising:
   obtaining information indicative of the topography of a surface of the substrate, wherein the obtaining comprises:
      directing a beam of radiation at the surface of the substrate, the topography comprising a recess and/or protrusion of the surface,
      detecting angular or spatial changes in intensity distribution, or changes in angle of reflection, of the beam of radiation after the beam of radiation has been reflected from the surface of the substrate, and
      determining information indicative of the height relative to the surface, or size, of the topography of the surface of the substrate from the extent and/or rate of change of the detected changes in intensity distribution or angle of reflection; and using the information indicative of the topography of the substrate to define a plurality of grid sections, each grid section being associated with an area of the substrate to which the pattern is to be applied, and each grid section having associated with it:

a set of exposure conditions which are used to define a depth of focus for that grid section, a peak-to-valley variation in the topography of the area of the substrate associated with a grid section being encompassed by the depth of focus for that grid section; or a substrate position or orientation which is used to control the position or orientation of the substrate such that the area of the substrate to which the pattern is to be applied is within a given depth of focus; and applying a pattern to the substrate in accordance with the exposure conditions, or substrate positions or orientations, defined by the grid sections.

16. The method of claim 15, wherein the grid sections form a plurality of grid section sets and each different grid section set of the plurality is associated with different a set of exposure conditions, or substrate positions or orientations, and further comprising applying the pattern to the substrate in accordance with the grid section sets.

17. The method of claim 16, wherein areas of the substrate associated with grid sections of a grid section set are patterned before areas of the substrate associated with grid sections of another grid section set.

18. The method of claim 16, wherein the grid sections are square or rectangular in shape.

19. The method of claim 15, wherein the substrate is a flexible substrate.

20. The method of claim 19, wherein the flexible substrate comprises a metal foil or a plastic sheet.

21. An apparatus, comprising:

an electromagnetic radiation source arranged to provide a beam of radiation in a direction of a surface of a substrate, the topography of the substrate comprising a recess and/or protrusion of the surface;

an electromagnetic radiation detector configured to detect angular or spatial changes in intensity distribution, or changes in angle of reflection, of at least a part of the beam of radiation after it has been reflected from the surface of the substrate;

a processing system configured to determine information indicative of the height relative to the surface, or size, of the topography of the surface of the substrate from the extent and/or rate of change of the detected changes in intensity distribution or angle of reflection; and a control system for use in or with a lithographic apparatus, the controller being arranged to take into account a plurality of grid sections which have been defined using the information indicative of the topography of the substrate, each grid section being associated with an area of the substrate to which the pattern is to be applied, and each grid section being associated with:

a set of exposure conditions which are used to define a depth of focus for that grid section, a peak-to-valley variation in the topography of the area of the substrate associated with a grid section being encompassed by the depth of focus for that grid section; or a substrate position or orientation which is used to control the position or orientation of the substrate such that the area of the substrate to which the pattern is to be applied is within a given depth of focus;

the controller being arranged to control the apparatus to apply a pattern to the substrate in accordance with the exposure conditions, or substrate positions or orientations defined by the grid sections.

* * * * *